US007446131B1

(12) United States Patent
Liu et al.

(10) Patent No.: US 7,446,131 B1
(45) Date of Patent: Nov. 4, 2008

(54) POROUS POLYMERIC MATRICES MADE OF NATURAL POLYMERS AND SYNTHETIC POLYMERS AND OPTIONALLY AT LEAST ONE CATION AND METHODS OF MAKING

(75) Inventors: LinShu Liu, Wyndmoor, PA (US); Marshall L. Fishman, Lansdale, PA (US); Kevin B. Hicks, Malvern, PA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 392 days.

(21) Appl. No.: 11/058,034

(22) Filed: Feb. 15, 2005

Related U.S. Application Data

(60) Provisional application No. 60/578,618, filed on Jun. 10, 2004, provisional application No. 60/613,936, filed on Sep. 28, 2004.

(51) Int. Cl.
*C08B 37/00* (2006.01)
(52) U.S. Cl. .............................. 521/61; 521/62; 521/64; 521/84.1; 521/92; 521/138; 424/422; 514/54
(58) Field of Classification Search .................. 521/61, 521/62, 64, 84.1, 92, 138; 424/422; 514/54
See application file for complete search history.

(56) References Cited

U.S. PATENT DOCUMENTS

| | | | |
|---|---|---|---|
| 4,060,081 A | 11/1977 | Yannas et al. | 623/15.12 |
| 5,041,138 A | 8/1991 | Vacanti et al. | 424/422 |
| 5,514,378 A | 5/1996 | Mikos et al. | 424/425 |
| 5,677,276 A | 10/1997 | Dickerson et al. | 514/8 |
| 5,744,516 A | 4/1998 | Hashitani et al. | 523/124 |
| 5,817,728 A | 10/1998 | Higuchi et al. | 527/300 |
| 6,010,870 A | 1/2000 | Pelzer et al. | 435/41 |
| 6,114,496 A | 9/2000 | Otera et al. | 528/361 |
| 6,124,384 A | 9/2000 | Shiraishi et al. | 524/35 |
| 6,150,438 A | 11/2000 | Shiraishi et al. | 524/35 |
| 6,207,749 B1 | 3/2001 | Mayes et al. | 524/731 |
| 6,294,202 B1 | 9/2001 | Burns et al. | 424/488 |
| 6,350,531 B1 | 2/2002 | Sugimoto | 428/533 |
| 6,379,962 B1 | 4/2002 | Holy et al. | 435/395 |
| 6,388,047 B1 | 5/2002 | Won et al. | 528/354 |
| 6,399,700 B2 | 6/2002 | Mayes et al. | 524/731 |
| 6,423,345 B2 | 7/2002 | Bernstein et al. | 424/501 |

OTHER PUBLICATIONS

LinShu Liu , Pectin/poly(lactide-co-glycolide) composite matrices for biomedical applications , Biomaterials vol. 25, Issue 16, Jul. 2004, pp. 3201-3210 , Available online Nov. 21, 2003.*
Voragen, A.G.J., et al., "Determination of the Degree of Methylation and Acetylation of Pectins by h.p.l.c.", *Food Hydrocolloids*, vol. 1(1), pp. 65-70, 1986.
Temenoff, J.S., et al., "Review: Tissue Engineering for Regeneration of Articular Cartilage", *Biomaterials*, vol. 21, pp. 431-440, 2000.
Smith, P.K., et al., "Measurement of Protein Using Bicinchoninic Acid", *Analytical Biochemistry*, vol. 150, pp. 76-85, 1985.

Semde, R., et al., "Studies of Pectin HM/Eudragit® RL/Eudragit® NE Film-Coating Formulations Intended for Colonic Drug Delivery", *International Journal of Pharmaceutics*, vol. 197, pp. 181-192, 2000.
Rubinstein, A., et al., In Vitro Evaluation of Calcium Pectinate: A Potential Colon-Specific Drug Delivery Carrier, *Pharmaceutical Research*, vol. 10(2), pp. 258-263, 1993.
Schols, H.A., et al., Complex Pectins: Structure Elucidation Using Enzymes, In: *Pectin and Pectinases*, J. Visser and A.G.J. Vorangen, editors, Elsevier Science, Amsterdam, pp. 3-19, 1996.
Ouchi, T., et al., "Preparation of Poly (L-lactide)-Based Microspheres Having a Cationic or Anionic surface Using Biodegradable Surfactants", *Macromolecules*, vol. 3(5), pp. 885-888, 2002.
Nilsson, K., et al., "Immobilization of Enzymes and affinity Ligands to Various Hydroxyl Group Carrying Supports Using Highly Reactive Sulfonyl Chlorides", *Biochemical and Biophysical Res. Communications*, vol. 102(1), pp. 449-457, Sep. 16, 1981.
Mikos, A.G., et al., "Preparation and Characterization of Poly (L-lactic acid) foams", *Polymer*, vol. 35(5), pp. 1068-1077, 1994.
Liu, L., et al., "Pectin-Based Systems for Colon-Specific Drug Delivery Via Oral Route", *Biomaterials*, vol. 24, pp. 3333-3343, 2003.
Massia, S.P., et al., "Covalent Surface Immobilization of Arg-Gly-Asp- and Tyr-Ile-Gly-Ser-Arg- Containing Peptides to Obtain Well Defined Cell-Adhesive Substrates", *Analytical Biochemistry*, vol. 187, pp. 292-301, 1990.
Ma, P.X., et al., "Engineering New Bone Tissue in vitro on Highly Porous Poly($\alpha$-hydroxyl acids) /Hydroxyapatite Composite Scaffolds", *Biomed. Mater. Res.*, vol. 54(2), pp. 284-293, 2001.
Liu, L., et al., "Pectin/Poly(lactide-co-glycolide) Composite Matrices for Biomedical Applications", *Biomaterials*, vol. 25, pp. 3201-3210, Jul. 2004.

(Continued)

*Primary Examiner*—Irina S Zemel
(74) *Attorney, Agent, or Firm*—John D. Fado; G. Byron Stover

(57) ABSTRACT

A porous polymeric matrix containing at least one natural polymer and at least one synthetic polymer and optionally at least one cation. Furthermore, a method of making a porous polymeric matrix involving mixing at least one natural polymer and inorganic salts with a solution comprising at least one solvent and at least one synthetic polymer to form a slurry, casting the slurry in a mold and removing the solvent to form solid matrices, immersing the solid matrices in deionized water to allow natural polymer cross-linking and pore creation to occur simultaneously, and drying the matrices to create a porous polymeric matrix; wherein the matrix contains a cation. Also, a method of making a porous polymeric matrix, involving mixing at least one natural polymer in an aqueous solvent and mixing at least one synthetic polymer in an organic solvent, combining the mixtures and casting in a mold, and separately removing said aqueous solvent and said organic solvent to form a porous polymeric matrix; wherein the porous polymeric matrix does not contain a cation.

18 Claims, 11 Drawing Sheets

OTHER PUBLICATIONS

Langer, R., et al., "Tissue Engineering", *Science*, vol. 260, pp. 920-926, 1993.

Liu, L. et al., "Conversion of Pectin and Related Polysaccharides into Unique Biomaterials for Biomedical Applications", *Proceedings of the United States-Japan UJNR Cooperative Program in Natural resources and Agricultural Panel, 32nd Annual Meeting, Tsukuba, Ibaraki, Japan*, pp. 405-409, Nov. 9-15, 2003.

Liu, L., et al., "Adhesion Barriers of Carboxymethylcellulose and Polyethylene Oxide Composite Gels", *Biomed. Mater. Res, (Appl. Biomater.)*, vol. 63, pp. 326-332, 2002.

Ishaug, S., et al., "Bone Formation by Three-Dimensional Stromal Osteoblast Culture in biodegradable Polymer Scaffolds", *J. Biomedical Materials Res.*, vol. 36, pp. 17-28, 1997.

Hwang, J., et al., "Structure and Rheological Function of Side Branches of Carbohydrate Polymers", *J. Texture Studies*, vol. 22, pp. 123-167, 1991.

Fishman, M., et al., "Characterization of Pectin, Flash-Extracted from Orange Albedo by Microwave Heating, Under Pressure", *Carbohydrate Res.*, vol. 323, pp. 126-138, 2000.

Fishman, M., et al., "Solvent Effects on the Molecular Properties of Pectins", *J. Agric. Food Chem.*, vol. 49, pp. 4494-4501, 2001.

Dubois, M., et al., "Colorimetric Method for Determination of Sugars and Related Substances", *Anal. Chem.*, vol. 28(3), pp. 350-356, Mar. 1956.

Coffin, D., et al., Thermomechanical Properties of Blends of Pectin and Poly(vinyl alcohol), *Appl. Polym. Science*, vol. 61, pp. 71-79, 1996.

Chen, C., et al., "Geometric Control of Cell Life and Death", *Science*, vol. 276, pp. 1425-1428, May 30, 1997.

Berthold, A., et al., "Preparation and Characterization of Chitosan Microspheres as Drug Carrier for Prednisolone Sodium Phosphate as Model for Anti-Inflammatory Drugs", *J. Controlled Release*, vol. 39, pp. 17-25, 1996.

BeMiller, J.N., "An Intoduction to Pectins: Structure and Properties", In: *Chemistry and Function of Pectins, ACS Series310, M.L. Fishman and J.J. Jen, editors, American Chemical Society, Washington, D.C.*, pp. 2-13, 1986.

\* cited by examiner

A    B

POROUS POLYMERIC MATRICES MADE OF NATURAL POLYMERS AND SYNTHETIC POLYMERS AND OPTIONALLY AT LEAST ONE CATION AND METHODS OF MAKING

REFERENCE TO RELATED APPLICATION

This application claims the benefit of U.S. Provisional Application No. 60/578,618, filed 10 Jun. 2004, and U.S. Provisional Application No. 60/613,936, filed 28 Sep. 2004, which are incorporated herein by reference in their entirety.

BACKGROUND OF THE INVENTION

The present invention relates to a porous polymeric matrix containing at least one natural polymer and at least one synthetic polymer and optionally at least one cation. Furthermore, the present invention relates to a method of making a porous polymeric matrix involving mixing at least one natural polymer and inorganic salts with a solution containing at least one solvent and at least one synthetic polymer to form a slurry, casting the slurry in a mold and removing the solvent to form solid matrices, immersing the solid matrices in deionized water to allow natural polymer cross-linking and pore creation to occur simultaneously, and drying the matrices to create a porous polymeric matrix; wherein the matrix contains a cation. Also, a method of making a porous polymeric matrix, involving mixing at least one natural polymer in an aqueous solvent and mixing at least one synthetic polymer in an organic solvent, combining the mixtures and casting in a mold, and separately removing said aqueous solvent and said organic solvent to form a porous polymeric matrix; wherein the porous polymeric matrix does not contain a cation.

Polymers such as poly(lactide-co-glycolide)(p(LGA)) has been used clinically for tissue repair and organ regeneration for decades. Poly(lactide-co-glycolide), a hydrophobic polymer, is biocompatible, biodegradable, and easily processed into a variety of sizes and shapes which have good mechanical properties (Ma, P. X., and R. Langer, Fabrication of biodegradable polymer foams for cell transplantation and tissue engineering, In: Tissue engineering methods and protocols, J. Morgan and M. Yarmush, editors, Humana Press Inc., Totowa, N.J., 1999, p. 47-56; Lanza, R. P., et al., Principles of tissue engineering, Academic Press, San Diego, Calif., 1997; Patrick, C. W., et al., editors, Frontiers in tissue engineering, Pergamon, N.Y., 1998; Ma, P. X., et al., J. Biomed. Mater. Res., 54(2): 284-93 (2001)). Although p(LGA) will support cell attachment and cell growth, it does not impart signals to the cells (Langer, R., J. P. Vacanti, Science, 260: 920-6 (1993)). The inability to carry signal molecules limits the application of polymers such as p(LGA). This deficiency is currently overcome by synthesizing block or graft copolymers of lactic acid and lysine or other segments carrying side chain functional groups (Langer, R., J. P. Vacanti, Science, 260: 920-6 (1993); Ouchi, T. et al, Macromolecules, 3(5): 885-8 (2002)). Through the functional groups, specific amino acid sequences can be attached. By this strategy, a number of new chemical entities have been provided. However, the preparation of such copolymers involves a series of cumbersome isolation, purification and identification procedures.

The present invention provides matrices, made of natural polymers (e.g., pectins) and synthetic polymers such as p(LGA) and optionally at least one cation, that retain the biomechanical strength of polymers such as p(LGA) yet also provide access for hydrophilic, bioactive substances.

SUMMARY OF THE INVENTION

In accordance with the present invention there is provided a porous polymeric matrix containing at least one natural polymer and at least one synthetic polymer and optionally at least one cation. Furthermore, in accordance with the present invention there is provided a method of making a porous polymeric matrix involving mixing at least one natural polymer and inorganic salts with a solution containing at least one solvent and at least one synthetic polymer to form a slurry, casting the slurry in a mold and removing the solvent to form solid matrices, immersing the solid matrices in deionized water to allow natural polymer cross-linking and pore creation to occur simultaneously, and drying the matrices to create a porous polymeric matrix; wherein the matrix contains a cation. Also, a method of making a porous polymeric matrix, involving mixing at least one natural polymer in an aqueous solvent and mixing at least one synthetic polymer in an organic solvent, combining the mixtures and casting in a mold, and separately removing said aqueous solvent and said organic solvent to form a porous polymeric matrix; wherein the porous polymeric matrix does not contain a cation.

DETAILED DESCRIPTION OF THE INVENTION

Figure 1:
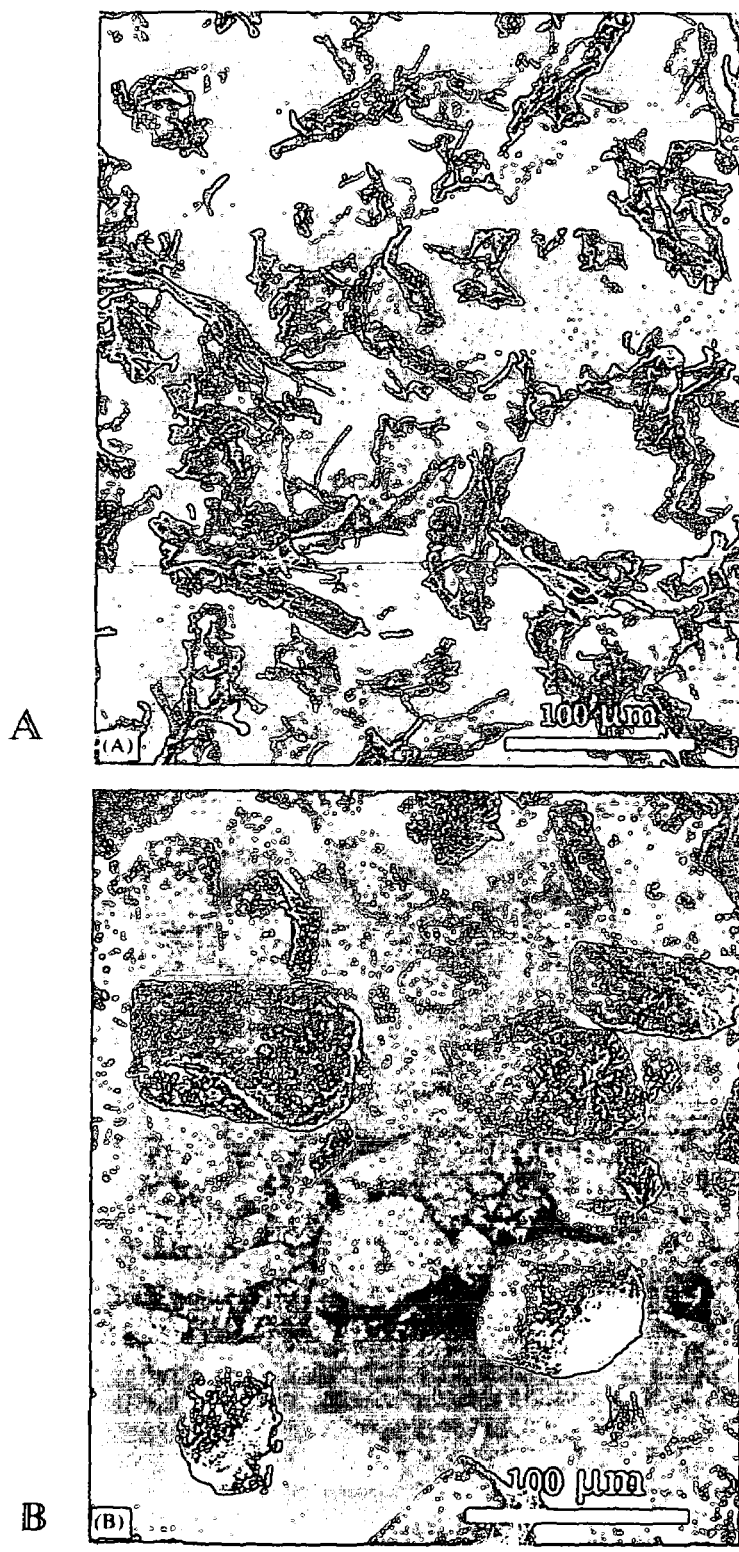
FIG. 1 shows SEM photographs of (A) pectin particles and (B) NaCl—$CaCl_2$ mixtures (bar=100 μm).

The present invention relates to a porous polymeric matrix containing at least one natural polymer and at least one synthetic polymer and optionally at least one cation. Furthermore, the present invention relates to a method of making a porous polymeric matrix involving mixing at least one natural polymer and inorganic salts with a solution comprising at least one solvent and at least one synthetic polymer to form a slurry, casting the slurry in a mold and removing the solvent to form solid matrices, immersing the solid matrices in deionized water to allow natural polymer cross-linking and pore creation to occur simultaneously, and drying the matrices to create a porous polymeric matrix; wherein the matrix contains a cation. Also, a method of making a porous polymeric matrix, involving mixing at least one natural polymer in an aqueous solvent and mixing at least one synthetic polymer in an organic solvent, combining the mixtures and casting in a mold, and separately removing said aqueous solvent and said organic solvent to form a porous polymeric matrix; wherein the porous polymeric matrix does not contain a cation.

The present invention provides three-dimensional porous matrices (scaffolds) made of natural polymers such as pectin and water insoluble synthetic polymers such as p(LGA) and optionally at least one cation. The matrices retain the biomechanical strength of the synthetic polymers, such as p(LGA), yet provides access for hydrophilic, bioactive substances.

The synthetic polymers which may be utilized in the present invention may be non-biodegradable or biodegradable synthetic water insoluble polymers. The biodegradable polymers may be polyesters, polyanhydrides, or polyortho esters. Representative polyesters include poly(lactic acid), poly(glycolic acid), and poly(lactic acid-co-glycolic acid), poly(lactide) [p(LA)], poly(glycolide) [p(GA)], poly(lactide-co-glycolide) [p(LGA)], polycaprolactone and poly(lactide-co-caprolactone). The preferred polyester is p(LGA). Representative polyanhydrides include poly(carboxyphenoxy propane-sebacic acid) [p(CPP/SA), CPP:SA=20:80 and 50:50], poly[1,6-bis(p-carboxyphenoxy)hexane [p(CPH)], and poly(anhydride-co-imide), the preferred polyanhydride is p(CPP/SA). Representative polyortho esters include the polyortho esters prepared by condensation polymerization of 3,9-diethylidene-2,4,8,10-tetraoxaspiroundecane (DETOSU) and the diols containing trans-cyclohexanedimethanol, triethylene glycol or N-methyldiethanolamine, and their copolymers with p(LGA) or polyethylene glycol; the preferred polyortho esters are their copolymer containing p(LGA). Other biodegradable polymers include polyamides, such as polypeptides; poly(butyric acid), poly(valeric acid), and their copolymers, polyalkylene glycols such as poly(ethylene glycol), polyalkylene oxides such as poly(ethylene oxide). Non-biodegradable polymers include polyalkylene terepthalates such as poly(ethylene terephthalate), polyvinyl alcohols, polyvinyl halides such as poly(vinyl chloride), polyvinylpyrrolidone, polysiloxanes, poly(vinyl acetate), polystyrene, polyurethanes, polycarbonates, polyalkylenes such as polyethylene and polypropylene, and copolymers thereof. Polymers of acrylic acid, methacrylic acid or copolymers or derivatives thereof including, poly(methyl methacrylate), poly(ethyl methacrylate), poly(butyl-methacrylate), poly(isobutyl methacrylate), poly(hexyl-methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate) jointly referred to herein as "polyacrylic acids"), and blends thereof. As used herein, "derivatives" include polymers having substitutions, additions of chemical groups, for example, alkyl, alkylene, hydroxylations, oxidations, and other modifications routinely made by those skilled in the art.

Preferably the synthetic polymer is poly(lactide-co-glycolide) with any MW or MW polydispersity, all ratios between lactic acid (LA) and glycolic acid (GA), and all degrees of crystallinity. Generally, the MW ranges from about 500 to about 10,000,000 Da, preferably from about 2,000 to about 1,000,000 Da, and more preferably from about 500 to about 5,000 Da. The p(LGA) with the ratio of LA:GA at about 75:25 to about 85:15 (mol:mol) and the MW from about 5,000 to about 500,000 are preferred for matrices designed for all tissue repair, especially for bone repair.

Representative natural polymers and their derivatives include the following: proteins such as albumin and polysaccharides such as pectin, chitosan, hyaluronate esters, polyhydroxybutyrate, cellulose and derivativized celluloses such as alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt (jointly referred to herein as "synthetic celluloses"). Preferably the natural polymer is pectin; the molecular weight (MW) range of pectin used depends on the degree of pectin esterification (DE; a designation of the percent of carboxyl groups esterified with methanol). Generally the MW of the pectin ranges from about 500 to about 1,000,000 Da (preferably from about 230,000 to about 280,000 Da; more preferably about 3000 Da); MW of pectin was measured by high performance size exclusive chromatography (HPSEC) equipped with on-line multi-angle laser light scattering and viscometric detection (Fishman, M. L., et al., J. Agr. Food Chem., 49: 4494-4501 (2001)). Generally the DE ranges from about 10 to about 100% (preferably from about 25 to about 76%; more preferably from about 25 to about 35%).

A solvent for the polymer is selected based on its biocompatibility as well as the solubility of the polymer and where appropriate, interaction with the agent to be delivered. For example, the ease with which the agent is dissolved in the solvent and the lack of detrimental effects of the solvent on the agent to be delivered are factors to consider in selecting the solvent. Aqueous solvents can be used to make matrices formed of water-soluble polymers. Organic solvents will typically be used to dissolve hydrophobic and some hydrophilic polymers. Preferred organic solvents are volatile or have a relatively low boiling point or can be removed under vacuum and which are acceptable for administration to humans in trace amounts, such as methylene chloride. Other solvents, such as ethyl acetate, ethanol, methanol, dimethyl formamide (DMF), acetone, acetonitrile, tetrahydrofuran (THF), acetic acid, dimethyl sulfoxide (DMSO) and chloroform, and combinations thereof, also may be utilized. Preferred solvents are those rated as class 3 residual solvents by the Food and Drug Administration, as published in the Federal Register vol. 62, number 85, pp. 24301-24309 (May 1997). Dichloromethane is preferably used with polylactide-co-glycolide.

In general, the polymer is dissolved in the solvent to form a polymer solution having a concentration of between 0.1 and 60% weight to volume (w/v), more preferably between 0.25 and 30%. The polymer solution is then processed as described below to yield a polymer matrix.

Generally, the matrices are produced by a novel method involving the following:

(a) Dispersing at least one natural polymer (e.g., pectin) and inorganic salt particles into a solution containing at least one synthetic polymer and at least one solvent (e.g., p(LGA)/dichloromethane) and mixing well to form a slurry; generally at a temperature of from about 4 to about 37° C. (preferably from about 10 to about 27° C.; more preferably at about 20° C.) and for about 1 to about 30 minutes (preferably from about 3 to about 20 minutes; more preferably from about 3 to about 5 minutes). The ratio of the salt particles and natural polymer (e.g., pectin) to the synthetic polymer (e.g., p(LGA)) ranges from about 1:1 to about 40:1 (preferably about 20:1, more preferably about 9:1 (w/w). The inorganic salts used are dependant on the type of natural polymer utilized; generally the inorganic salt may be calcium chloride, sodium chloride, magnesium chloride, sodium sulfate, potassium sulfate, ammonium sulfate, ammonium chloride, potassium chloride, or others known in the art. For example, with pectin the salts may be calcium chloride or a mixture of calcium chloride and sodium chloride or a mixture of magnesium chloride and sodium chloride; preferably calcium chloride and/or sodium chloride. Sodium nitrate, potassium nitrate, or magnesium nitrate many be used with calcium chloride when the natural polymer is pectin or alginate or hyaluronate or carboxy methyl cellulose. The ratio of natural polymer (e.g., pectin) to salt generally ranges from about 1:about 0.1-about 20 (preferably about 1:15, more preferably about 1:about 10). The size of natural polymers (e.g., pectin) and salt particles are generally about 20 to about 300 microns (preferably about 30 to about 250 microns; more preferably about 50 to about 200 microns).

(b) Casting the slurry in a mold and removing the solvent by evaporation (or by other methods known in the art) to form solid matrices (generally at a temperature of from about 4 to about 37° C., preferably from about 10 to about 27° C., preferably at about 20° C.; generally bench+vacuum ranges from (12 to 24)+(2 to 8), more preferably (18 to 20)+(2 to 4), more preferably 18+4).

(c) Immersing the solid matrices in a large volume of deionized (DI) water thus allowing pectin cross-linking and pore creation to occur simultaneously (generally at room temperature). The amount of DI water is generally from about 0.5 to about 50 L (preferably about 0.5 to about 40 L, more preferably about 0.5 L) and the volume of matrix is generally from about 1 to about 10 ml (preferably about 2 to about 8 ml, more preferably about 5 ml).

(d) Drying (e.g., freeze drying or by other methods known in the art) the matrices to create a channeled porous structure. Generally freeze drying is utilized at a temperature from about –5 to about –70° C. (preferably about –10 to about –50° C., more preferably about –20° C.).

The ratio of natural polymer (e.g., pectin) to synthetic polymer is flexible and generally ranges from about 0.1:about 99.9 to about 99.9:about 0.1 (pectin:polymer); about 5-about 15 parts of pectin to about 100 parts of polymer is preferred.

Suitable applications for the present matrices (scaffolds) will vary with polymer composition and structure. For example, biodegradable polymer scaffolds are suitable for use in either in vitro applications and/or in vivo cell transplantation. The matrices may serve then as supports or scaffolds to allow cell growth to occur in vitro prior to implantation in vivo. The scaffolds may also be used directly in vivo, without being pre-seeded with cells. In both applications (with or without prior cell seeding), biodegradable polymer matrices in accordance with the present invention are particularly useful for the growth of three-dimensional tissue and may be used in the growth of connective tissues, like bone, cartilage, paradontal tissue, as well as dental tissues and other organs, such as liver or breast tissue.

For example, any desired cell type may be cultured in vitro in the presence of one of the matrices of the present invention to form a matrix that is coated, impregnated or infiltrated with the cells. Preferably, the cells are derived from a mammal, and most preferably from a human. In one example, fibroblast infiltrated matrices may be placed at the site of a skin lesion (e.g., wound or ulcer) to promote healing of the lesion. Other cell types that can be cultured on the matrices of this invention include but are not limited to, osteocytes, chondrocytes, keratinocytes, and tenocytes. Matrices impregnated with these cells can be used to aid in the healing of bone, cartilage, skin, and tendons and ligaments, respectively. Matrices can also be generated which contain a mixture of cell types, e.g., to mimic the cellular makeup of a desired tissue. The matrices of this invention can also be seeded with non-differentiated mesenchymal cells that can differentiate into a variety of tissue specific types upon implantation, or seeded with fetal or neonatal cells of the desired type. One advantage associated with the use of the cellular matrices in vivo is that the matrix is completely biocompatible and is reabsorbed by the body. Alternatively, matrices impregnated with various cell types are useful for in vitro diagnostic applications. For example, matrices infiltrated with fibroblasts can be used to test the efficacy and/or toxicity of various pharmaceutical or cosmetic compounds.

In one aspect, the invention features a method for promoting cell growth and proliferation in vitro. In this aspect, the method includes the steps of obtaining a sample of cells, admixing the cells with the matrices described herein, and then culturing the admixture under conditions sufficient to promote growth and infiltration of the cells into the matrix. Cells which may be grown according to the method of the invention include any cell type which can be cultured in vitro; preferably, the cells are mammalian; and most preferably, they are derived from a human.

In still another aspect, the invention includes a method for promoting cell growth and proliferation in vivo at the site of an injury, e.g., in a mammal, preferably a human. This method includes the steps of obtaining a sample of cells capable of promoting healing of the injury, admixing the cells with the matrices described herein, and placing the admixture at the site of injury in the mammal to promote growth and proliferation of cells at the site in order to facilitate the healing of the injury.

Embodiments of this aspect of the invention include obtaining the cell sample directly from the desired tissue and admixing the sample with the matrices described herein; obtaining the cell sample from the desired tissue and culturing the cells in vitro prior to admixture with the matrices described herein; and obtaining the cell sample from an established cell line and admixing the cells with the matrices described herein. Preferably, the admixture containing the cell sample and the matrix is cultured in vitro under conditions sufficient to promote proliferation and infiltration of the cells into the matrix prior to placement at the site of injury.

The cells admixed with the matrix for this aspect of the invention can be of any cell type which is capable of supporting cell growth and proliferation at the site of injury. For example, the source of the cells can be xenogeneic to the mammal, but preferably the cells are allogeneic, and most preferably the cells are immunologically compatible with the mammal. Further, the infiltrated matrix can contain cells of the same cell type as the cells found at the site of injury (e.g., from the same tissue), or the matrix can contain cells which are of a different cell type but which deposit extracellular matrix components within the matrix to serve as a scaffold for cell growth in vivo.

In preferred embodiments of this aspect of the invention, the cells are fibroblasts and the infiltrated matrix is placed at the site of a skin lesion (e.g., a wound, burn, surgical incision, or a dermal ulcer), the cells are osteocytes, and the infiltrated matrix is placed at the site of a bone injury; the cells are chondrocytes and the infiltrated matrix is placed at the site of an injury to cartilaginous tissue; the cells are keritinocytes and the infiltrated matrix is placed at the site of a skin lesion; the cells are tenocytes and the infiltrated matrix is placed at the site of an injury to a tendon; or the cells are non-differentiation mesenchymal cells.

The matrices of the invention may further include a drug for use as a drug delivery system. The particular drug used is a matter of choice depending on the intended use of the composition. Preferred drugs include, but are not limited to, proteins (e.g., growth factors, enzymes), steroids, non-steroidal anti-inflammatory drugs, cytotoxic agents (e.g., anti-tumor drugs), antibiotics, oligonucleotides (e.g., antisense), and biopolymers. When provided for cell and tissue growth and proliferation, the matrices of the invention may further include growth factors, and cell attachment proteins or peptides.

The matrix used in the methods of the invention can further contain one or more drugs, e.g., a growth factor to further enhance growth of the cells and/or an antibiotic to reduce the risk of infection at the site of placement. Active agents which can be incorporated into the matrix for delivery include therapeutic or prophylactic agents. These can be proteins or peptides, sugars, oligosaccharides, nucleic acid molecules, or other synthetic or natural agents. The agents may be labeled with a detectable label such as a fluorescent label or an enzymatic or chromatographically detectable agent. Preferred drugs include antibiotics, antivirals, vaccines, vasodilators, vasoconstrictors, immunomodulatory compounds, including steroids, antihistamines, and cytokines such as interleukins, colony stimulating factors, tumor necrosis factor and interferon (alpha, beta, gamma), oligonucleotides including genes and antisense, nucleases, bronchodilators, hormones including reproductive hormones, calcitonin, insulin, erythropoietin, growth hormones, and other types of drugs such as Antiban™.

In another aspect, the invention features a porous polymeric matrix containing at least one natural polymer (e.g., described above) and at least one synthetic polymer (e.g., described above) without any organic or inorganic cross-linker or any divalent metal ions (e.g., calcium chloride). One method to make such a porous polymeric matrix involves mixing at least one natural polymer in an aqueous solution and at least one synthetic polymer in an organic solvent (e.g., described above) to form an emulsified system, casting the emulsified polymers in a mold and removing the more volatile solvent at one temperature and the other solvent at a higher temperature. For example, the solvents may be removed by lyophilization.

In general, a synthetic polymer (e.g., p(LGA)) is dissolved in a solvent to form a polymer solution having a concentration of between about 5% and about 20% (weight to volume, w/v) (e.g., 5-20%), preferably between about 10% and about 15% (w/v) (e.g., 10-15%), more preferably about 12.5% (w/v) (e.g., 12.5%); the molar ratio between the poly(lactic acid) and poly(glycolic acid) in the p(LGA) polymer is between about 20:80 to about 80:20 (e.g., 20:80-80:20), more preferably about 25:75 (e.g., 25:75). The natural polymer (e.g., pectin) is dissolved in an aqueous solution to form the second polymer solution having a concentration of between about 0.1% to about 10% (w/v) (e.g., 0.1%-10%), preferably between about 0.5% to about 5% (w/v) (e.g., 0.5%-5%), more preferably, about 2% (w/v) (e.g., 2%). The two polymer solutions are then processed as described below to yield a polymeric matrix.

Generally, the matrices are produced by a novel method involving the following: Mixing at least one natural polymer (e.g., pectin) solution and at least one synthetic polymer (e.g., p(LGA)) solution in a container; mixing may be done by vortexing, ultrasonic irradiation, homogenizing, stirring, shaking, rotating or other methods known in the art. Preferably, mixing is accomplished by vortexing at the highest speed for about 3 to about 5 minutes (e.g., 3-5 minutes). The ratio (volume/volume, v/v) of the two polymer solutions (e.g., pectin/p(LGA)) ranges from about 0.1:9.9 to about 9.9:0.1 (e.g., 0.1:9.9 to 9.9:0.1), preferably about 1:9 to about 9:1 (e.g., 1:9 to 9:1), more preferably about 1:3 (e.g., 1:3). The resulting emulsified mixture is immediately poured into a mold, which was pre-cooled in a bath containing dry ice and isopropyl alcohol, to freeze the mixture quickly.

After freezing, the mold with the contents is transferred into an icebox fully filled with dry ice and connected to a vacuum line. The vacuum removes the low molecular weight organic phase leaving the hydrophobic polymer(s) which are dispersed among the wet-ice phases. This procedure allows a network to form. The temperature in this step is controlled at between about $-70°$ C. to about $-40°$ C. ($-70°$ C. to $-40°$ C.), more preferably about $-50°$ C. (e.g., $-50°$ C.). Then, the temperature of the system is raised to between about $-20°$ C. to about $-5°$ C. (e.g., $-20°$ C. to $-5°$ C.), more preferably to about $-10°$ C. (e.g., $-10°$ C.), and the vacuum is continued at about $-10°$ C. (e.g., $-10°$ C.) for an additional time to remove the wet-ice phase; this step creates a second polymeric network which interpenetrates the first network.

The weight ratio of natural polymer (e.g., pectin) to synthetic polymer (e.g., p(LGA)) is flexible and generally ranges from about 0.2 parts of natural polymer (e.g., pectin) to about 99.8 parts of synthetic polymer (e.g., p(LGA) to about 94 parts of natural polymer (e.g., pectin) to about 6 parts of synthetic polymer (e.g., p(LGA)) (e.g., 0.2 parts of natural polymer to about 99.8 parts of synthetic polymer to 94 parts of natural polymer to 6 parts of synthetic polymer); preferably about 5 parts of natural polymer (e.g., pectin) to about 95 parts of synthetic polymer (e.g., p(LGA)) (e.g., 5 parts of natural polymer to 95 parts of synthetic polymer). Suitable applications for the present matrices (scaffolds) will vary with polymer composition and structure; specifically the matrices (scaffolds) may be used for soft tissue or cartilage or bone repair and regeneration.

The best conditions for pectin/p(LGA) matrix preparation are as follows: concentration of pectin 20 mg/ml; degree of esterification of pectin, 90%; concentration of p(LGA), 125 mg/ml; molar ratio between pLA and pGA, 75/25; volume ratio of pectin to p(LGA), 1:3; temperature slots, frozen at $-78°$ C., freeze-dry at $-50°$ C., then at $-10°$ C.

Several parameters enabled an interpenetrating matrix to form by the above method which does not utilize divalent metal ions (e.g., calcium chloride): (1) control of the concentration of the two polymeric solutions; (2) control of the volume ratio of the two polymeric solutions; (3) mixing (accomplished by vortexing, ultrasonic irradiation, homogenizing, stirring, shaking, rotating or by other methods); (4) environmental temperature control, minimally the method requires two different temperature slots to remove the two solvents by freeze-drying. Preferably, during removal of the first solvent by freeze-drying the second solvent should remain frozen. The combination of these parameters directly determine the degree of interpenetration of the two polymers, the thickness of strands in each polymeric networks, the porosity (pore volume, pore size and pore size distribution), and surface area. In combination these parameters indirectly determine other properties of the matrixes, such as mechanical properties, water stability, enzyme accessibility, mass diffusion and other responses to environmental stimuli.

The above method which does not utilize divalent metal ions (e.g., calcium chloride) can be employed to systems containing three, four or more types of polymers if these polymers can be dissolved in two or more solvents which are not miscible, or these polymers have different temperature-dependent solubility in the same solvent. Pure water can be added as the third phase and mixed with the system; the added pure water functions as a pore-forming reagent.

The two types of matrices are different in (1) composition: containing or not containing cross-linkers (e.g. calcium chloride), (2) structure: the natural polymer (e.g., pectin) was ionically cross-linked (e.g., by calcium for pectin) or the natural polymer is entrapped, (3) application: the first matrix containing cations is not suitable for cartilage generation but is designed for bone regeneration, while the second matrix without cations can be used for both bone and cartilage repair.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Example 1

Materials: Sodium salts of pectin from citrus fruits (degree of esterification, DE, 93%), bovine serum albumin (BSA), fluoresceinamine, p(LGA) [50:50; average $M_w$; 50,000-75,000; $T_g$ 45-50C], pectinase 3XL, neutral-buffered formalin, trypan blue, DNA Quantitation Kit, 2,2,2,-trifluoroethanesulfonyl chloride (tresyl chloride), and dimethylsulfoxide (DMSO) were purchased from Sigma-Aldrich (St. Louis, Mo.). Fetal bovine serum, α-minimum essential medium (α-MEM), ascorbic acid-free a-MEM (Formula 94-5049EL), penicillin-streptomycin, Dulbecco's phosphate-buffered saline, and trypsin-EDTA were purchased from Gibco BRL Products, Life Technologies (Grand Island, N.Y.). Ascorbic acid was purchased from Fisher Scientific (Pittsburgh, Pa.). Micro BCA® reagent was from Pierce (Rockford, Ill.). Ethylene oxide was purchased from H.W. Anderson Products (Chapel Hill, N.C.). All other chemicals were A.C.S. grade, and used without further purification.

De-esterification of pectins: Gentle alkaline de-esterification was performed by adjusting the pH of a pectin solution (1%, w/v) to 8.0 with 0.1N NaOH and stirring at 4° C. over 48 h (Rubinstein, A., et al., Pharm. Res., 10(2):258-63 (1993)). The reaction solution was dialyzed against a large volume of distilled water (DI water). Pectins were recovered by spreading the pectin solution into ethanol containing 0.1% $CaCl_2$, the resultant microparticles were filtered, washed with DI water, and lyophilized. Pectin particles with the size ranging from 15 to 125 μm were collected. The extent of de-esterification was determined by comparing the DE values of the de-esterified pectins with those before the reaction. The DE values of pectins were measured by high-performance liquid chromatography (HPLC) (Voragen, A. G. J., et al., Food Hydrocolloids, 1:65-70 (1986)). Other molecular properties of the de-esterified pectins, such as the weight average $M_w$; root mean square radius of gyration ($R_{gz}$); and intrinsic viscosity ([η]); were evaluated by HPSEC with on-line multi-angle laser light scattering and viscometric detection (Fishman, M. L., et al., Carbohydrate Res., 5:359-79 (2000)).

Preparation of Pectin/p(LGA) Composites: Pectin/p (LGA) Composite Matrices were prepared by a multi-step procedure. In step I, 1.0 g of p(LGA) was dissolved in 8.0 ml of chloroform, into which 0.10 g of de-esterified pectin, 2.0 g of calcium chloride, and 6.9 g of sodium chloride were dispersed and blended to form a slurry. The size of the inorganic salt particles ranged from 50 to 200 μm. In step II, the slurry was cast into disks in a mold with dimensions of 6 mm in diameter and 3 mm in thickness, and the solvent was evaporated to form a solid matrix. In step III, the matrix was immersed in 1 l of deionized water (DI water), where pectin particles started to swell and hydrate, salts began to dissolve and diffuse. Meanwhile, dissolved calcium ions reacted with and bound to the hydrated pectin particles via inter- and intra-chain chelation. Dissolved sodium chloride and excessive calcium salts diffused to create spaces for water migration. The process in step III was continued for 48 h. In that time the water was changed several times to complete cross-linking of pectin and leaching of residual salts. Lastly, freeze drying the matrices created a channeled porous structure.

Porous p(LGA) matrices were prepared by the same method as described above, except for the substitution of pectin with sodium chloride. Porous pectin matrices were prepared by casting pectin solution (2.0%, w/v) in a mold (6×3 mm (d×h)) lyophilizing the solution to create a solid structure, which thereafter was treated with calcium chloride solution (0.1 m) and lyophilized. The p(LGA) and pectin matrices were used as controls.

Recovery of p(LGA) and pectin from pectin/p(LGA) matrices: Samples were analyzed to determine the efficiency with which calcium chloride cross-linked pectin particles and the amounts of pectin and p(LGA) in the final composite matrices. Samples of pectin/p(LGA) matrices were vacuum-dried for 24 h prior to experimentation. Each dried sample was placed in 2.0 ml tetrahydrofuran (THF) in a volumetric flask equipped with a penny head stopper to prevent solvent evaporation. The mixture was continually shaken at low speed for 2 h to complete the extraction of p(LGA) polymers. The extraction solution was removed and analyzed for p(LGA) content using a Shimadzu HPLC equipped with an RID-10A refractive index detector and an SCL-10A data station (Model LC-10AD, Kyoto, Japan). An aliquot of the solution (10 ml) was injected and eluted by THF on a phenogel guard column (model 22824G, 50×7.8 mm, Phenomenex, Torrance, Calif.) and a phenogel column (model GP/4446, 300×7.8 mm, Phenomenex) at the flow rate of 0.5 ml/min. p(LGA)/THF solutions of known concentrations were run under the same conditions and used to prepare a standard curve.

After the removal of p(LGA) polymers, the solid residues, calcium cross-linked pectins, were washed with fresh THF (2×2 ml), dry ethanol (3×2 ml), and air-dried. Sodium phosphate solution (1.0 M, 2.0 ml, pH 6.5) was added to the flask which was sonicated to solubilize the pectin. Pectin content was analyzed by total sugar assay (Dubois, M., et al., Anal.

Chem., 28:350-6 (1956); Liu, L. S., and R. A. Berg, J. Biomed. Mater. Res. (Appl. Biomater.), 63:326-32 (2002)).

Chemical modification of pectin/p(LGA) matrices: The chemical modification of pectin/p(LGA) composite matrices was performed by grafting the matrices with fluoresceinamine using tresyl chloride as a coupling reagent (Nilsson, K., and K. Mosbach, Biochem. Biophys. Res. Comm., 102 (1):449-57 (1981); Dickerson, K. T., et al., U.S. Pat. No. 5,677,276). Samples of pectin/p(LGA) matrix were immersed in dry acetone (pre-dried over molecular sieve 4A; Acros, Pittsburgh, Pa.) for 24 h with three changes. To a glass vial containing 2.0 ml dry acetone and one piece of the dry sample, pyridine (200 ml) and tresyl chloride (100 ml) were added, and gently shaken for 10 min at room temperature. The sample was removed and rinsed with dry acetone (3×5 ml), phosphate-buffered saline (PBS) (pH 7.0, 2×5 ml), and placed in 2.0 ml of PBS (pH 7.8) containing fluoresceinamine (20 mm) and incubated for 20 h at room temperature. To completely remove the fluoreceinamine which was physically adsorbed rather than chemically conjugated, the sample was washed with 1 mM HCl and 0.2 M $NaHCO_3$ repeatedly, and 1.0 M NaCl containing 1 mM HCl, finally with DI water (U.S. Pat. No. 5,677,276). Samples thus treated were examined by confocal laser fluorescence microscopy as described in the following section.

P(LGA) matrices treated with both tresyl chloride and fluoreceinamine under the same conditions were used as controls.

Microscopic imaging. Scanning electron microscopy (SEM): For SEM examinations, samples of pectin particles, NaCl—$CaCl_2$ crystal mixtures, pectin/p(LGA), and p(LGA) matrices were mounted on specimen stubs, coated with a thin layer of gold in a sputter coating apparatus (Edwards High Vacuum, Wilmington, Mass.), and examined in a model JSM 840A scanning electron microscope (Jeol USA, Peabody, Mass.) operating at 10 kV in the secondary electron imaging mode. Images were collected at 25× and 250× using an Imix-1 digital image workstation (Princeton Gamma-tech, Princeton, N.J.). Confocal laser microscopy: Samples of fluorescently labeled pectin/p(LGA) composite matrices were glued to 1×3 inch microscope slides and placed in the sample stage of an IRBE optical microscope with a 10× lens integrated with a model TCS-SP laser scanning confocal microscope (Leica Microsystems, Exton, Pa.). The parameters for the image acquisition were set for confocal reflection (633 mm) and confocal fluorescence (488/500-530 nm) in two channels.

Dynamic mechanical analysis (DMA): Compressive mechanical testing of the matrices was performed on a Rheometric Scientific RSA II Solids Analyzer (Rheometric Scientific, Piscataway, N.J.) fitted with 25 mm parallel plates. Temperature control was maintained using a liquid nitrogen environmental controller. Each sample matrix was placed on the lower plate, the upper plate was lowered onto the sample to give a slight compressive force, and then locked in the place. The samples were tested using a compressive strain of 0.25-1.0%, depending on the stiffness of the sample. Storage modulus, loss modulus, and loss tangent were determined over a temperature range of −100° C. to +200° C. at the heating rate of 10° C./min. The data were analyzed using Rheometric Scientific Orchestrator software, version 6.5.7.

Determination of equilibrium water content and protein adsorption: Samples of pectin/p(LGA) and p(LGA) matrices were dried under vacuum at room temperature for 24 h. prior to the experiment. Each dried sample was incubated with a large volume of PBS (pH 7.0) at room temperature under gentle shaking. Samples were removed from the incubation solutions at intervals of 5, 15, 30, 45 min, and 1, 2, 4, 8 h., rinsed three times with DI water, wiped with tissue paper to remove the water adsorbed on the surfaces, and weighed ($W_w$): The samples were then re-dried under vacuum for 24 h. and weighed ($W_{rd}$): The water content of matrices at each time point was calculated: water content=$(W_w \times W_{rd})=W_w \times$ 100%.

The kinetics of protein adsorption in pectin/p(LGA) and p(LGA) matrices was studied by a procedure similar to that used for the determination of equilibrium water content, except for the addition of BSA (0.1%, w/v) in PBS. After rinsing with DI water, the samples were analyzed for the amount of protein adsorbed by protein BCA assay (Smith, P. K., Anal. Biochem., 150:76-85 (1985)). A series of BSA solutions with known concentrations were used to prepare a standard curve.

In vitro cell culture and bioassays: The potential for application of composite matrices in tissue engineering was evaluated in vitro by seeding and culturing osteoblast cells on the matrices. Osteoblasts (MC3T3-E1, clone 26) were thawed, cultured in a supplemented ascorbic acid-free α-MEM and 10% fetal calf serum (FBS) containing 100 U/ml penicillin and 100 mg/ml streptomycin in a humidified incubator at 37° C. with 5% $CO_2$. The medium was changed every other day. The cells of passages 3 and 4 were harvested, pelleted by centrifugation and re-suspended at the concentration of $2 \times 10^6$ cell/ml in α-MEM containing FBS (10%), antibiotics (1%), and L-ascorbic acid (50 mg/l) (complete medium). The viability of the cells was higher than 90% as determined with the trypan blue exclusion assay.

The pectin/p(LGA) and p(LGA) matrices were sliced into disks with dimensions of 6 mm in diameter and 1.5 mm in thickness, and sterilized in culture flasks with ethylene oxide for 2 days. The matrices were soaked in ethanol for 30 min, exchanged with PBS for three times for 30 min each time, then washed with the complete medium twice for 2 h each time.

For the cell attachment test, each of the matrices were placed in a teflon plate containing 0.5 ml of the cell suspension, cultured on an orbital shaker (Model 3520; Lab-Line Instrument, Melrose Park, Ill.) at 75 rpm under standard conditions. At day 3, the cell-loaded matrices were transferred into six-well tissue culture plates, 4 ml of complete medium were added into each well, cultured under standard conditions for 1 day. The matrices were removed from the medium, washed with PBS, fixed in 10% neutral-buffered formalin, dehydrated, and embedded in paraffin using standard procedures. Paraffin-embedded specimens were sectioned into 5-μm thick through the center, stained with hematoxylin and eosin, and examined under a light microscope (Lanza, R. P., et al., Principles of tissue engineering, Academic Press, San Diego, Calif., 1997; Carson, F. L., Histotechnology: a self instructional text, ASCP Press, Chicago, Ill., 1990).

For cell proliferation studies, the cell culture was continued for an additional 7 and 14 days. The medium was changed every other day. At the conclusion of cell culture, the matrices were removed, washed with PBS, homogenized using a polytron homogenizer (Brinkmann Easycare Generator; Polytron-Aggregate, Switzerland) for 30 s at top speed (VI) for three times, then subjected to DNA assay for cell number quantitation (Lanza, R. P., et al., Principles of tissue engineering, Academic Press, San Diego, Calif., 1997; Patrick, C. W., et al., editors, Frontiers in tissue engineering, Pergamon, N.Y., 1998). DNA assays were performed using DNA Quantitation Kit with Hoechst 33258 dye. The concentration of DNA in solution was converted to a cell number using a conversion factor of 7.8 pg of DNA per MC3T3-E1 cell. This conversion factor was determined by measuring the amount of DNA from a known cell number.

Statistical analysis: The data presented here are mean ±standard deviation. To test the significance of observed differences between the study groups, a paired Student's t-test was applied.

Results and discussion. De-esterification of pectin: Pectins were de-esterified prior to use for preparation of pectin/p (LGA) composite matrices. An almost complete de-esterification was accomplished (Table 1) to enable the insolubilization of pectin macromolecules by calcium ions. The $M_w$ and intrinsic viscosity of the pectin were slightly reduced after de-esterification in comparison with the original polymer (Table 1). In addition, $R_{gz}$ of pectin was reduced slightly after its de-esterification (Table 1). This indicated that some disaggregation and/or degradation of pectin macromolecules occurred during its de-esterification. Nevertheless, this seems to not significantly effect the binding efficiency of pectin to calcium ions since more than 80% of the pectin suspended in the p(LGA)/chloroform solution was recovered from the resulting pectin/p(LGA) matrices. Also the ratio of pectin to p(LGA) polymers was reduced only slightly after matrix fabrication (Table 2).

De-esterified pectins in the form of microparticles were collected and used for pectin/p(LGA) matrix preparation. The pectin particles showed some variations in size and morphology (FIG. 1A).

Preparation and microscopy of pectin/p(LGA) matrices: In the process described herein to prepare pectin/p(LGA) composite matrices, in one step the salt particles function passively as pore-creating reagents and simultaneously the salts play the additional role of a cross-linker, to bridge the highly de-esterified pectin particles. When a dry, solid matrix of polymer/salt was immersed in water, sodium chloride and calcium chloride dissolved quickly and diffused toward the surrounding liquid phase. Simultaneously, pectin molecules hydrated and swelled slowly as determined by its viscoelastic nature. Normally, the swelled pectin molecules would tend to dissolve and diffuse into the water phase but they were stopped by the cross-linking with calcium ions to form pectin-calcium hydrogels. The insolubilization of pectin was confirmed by analyzing it in the final matrix (Table 2).

Figure 2:
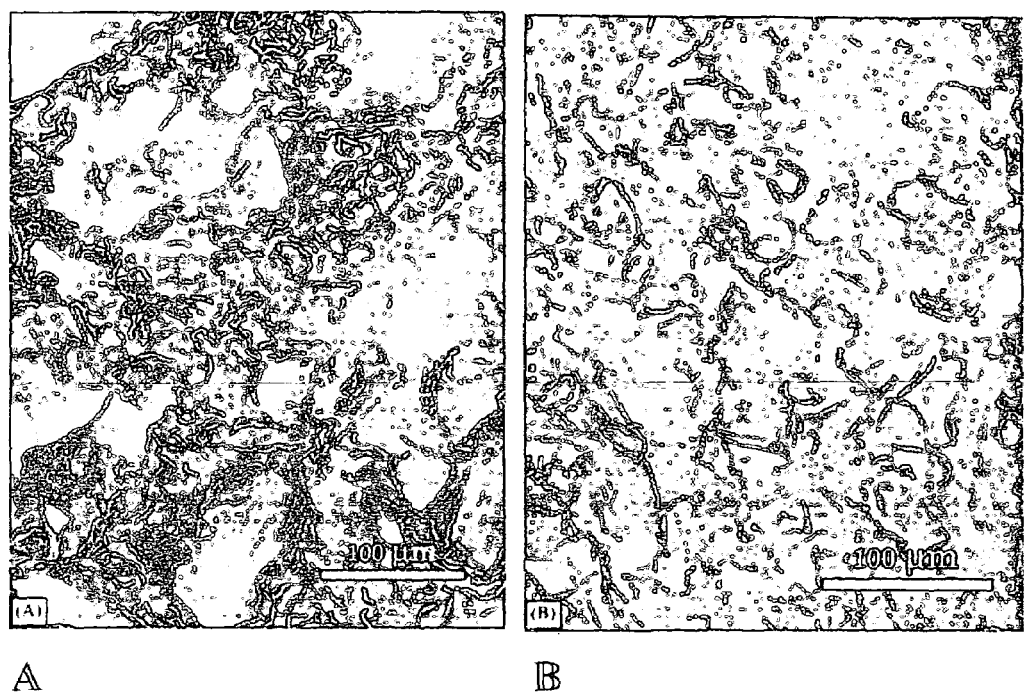
FIG. 2 shows (A) SEM images of p(LGA) matrix showing a continuous network of salt cavities with the size of 50-200 μm (bar=100 μm), (B) Pectin/p(LGA) composite matrix showing the leaf- or sheet-like pectin structures which stretched over all space (bar=100

The organization and microstructure of p(LGA) and pectin/p(LGA) matrices are illustrated in FIG. 2. Both matrices were porous and had a sponge-like morphology. Pores were evenly distributed into all areas of the matrices, and they were interconnected. The pores in p(LGA) matrices had sizes and shapes that matched those of the original salt crystals, as evidenced by SEM (FIGS. 1B and 2A). Pores and channels in p(LGA) matrices were lined by fibrils or flakes of p(LGA) polymers, indicating the deposition of p(LGA) polymers in the gaps or crevices among salt particles as the solvent evaporated. In this case, the microstructure and morphology of the matrices only depends on the weight ratio of salts/polymers and on the particle size of the salt.

Topographical, SEM images also revealed that the pores of the composite pectin/p(LGA) matrices were often smaller than the p(LGA) alone, and they were always lined or bordered by smooth, leaf-like surfaces (FIG. 2B). These surfaces resembled the appearance of the image texture of isolated pectin particles used to make the composite (FIG. 1A). Without being bound by theory, these images suggest that the p(LGA) forms a parenchymal matrix, binding the pectin particles which line the pores, together in the composite; nevertheless, it is difficult to localize the p(LGA) based on image features alone.

Pectin particles were covalently tagged with fluoresceinamine in order to locate areas of p(LGA) indirectly in the composite matrix. Confocal fluorescence and confocal reflection microscopy of the surfaces of composite matrices were used to resolve microscopically the integrated organization of the two components in correlated images. Reflection images (FIG. 3A) in stereo projection reveal the composite structure. A few flat areas of reflection coincided with areas of green fluorescence or pectin (FIG. 3B) which indicated that whether or not areas of pectin particles reflected light depended upon their orientation. Other areas of reflection, containing irregular tubes and anastomoses do not fluoresce, indicating that these areas contain p(LGA) (FIG. 3A).

Without being bound by theory, from the above observations it appears that the pectin domains not only filled in the pore spaces created by the deposition of p(LGA) polymers in gaps among particles, but also covered or wrapped most of the p(LGA) domains. In general, pectin/p(LGA) matrices presented a complex structure of connected porous pectin networks which were reinforced by p(LGA) networks.

Figure 4A:
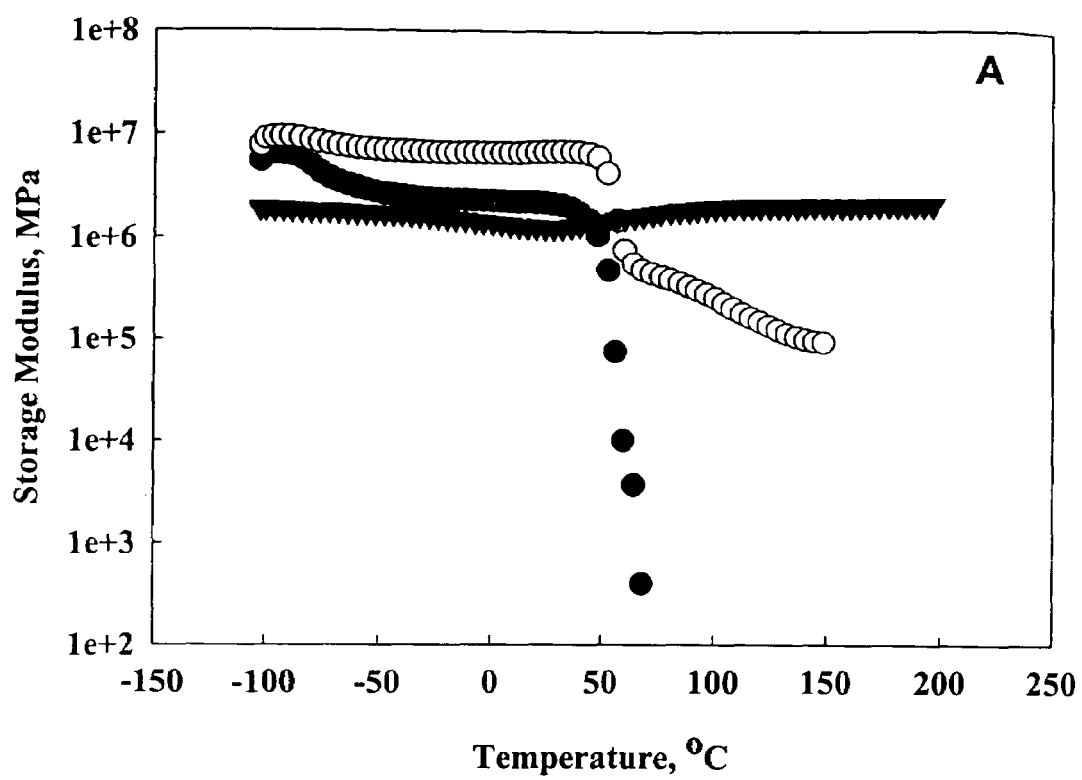
FIG. 4 shows typical plots of (A) storage modulus, (B) loss modulus, and (C) loss tangent as a function of temperature; the pectin/p(LGA) composite matrix (○) has higher storage modulus and loss modulus values than p(LGA) matrix (•) and pectin matrix (▼) in the −80° C. to −40° C. range; the p(LGA) matrix has a glass transition at about 50° C., above that the p(LGA) gives no force reading, in contrast some residual force still remained with pectin/p(LGA) matrix and pectin matrix; the loss tangent cures of all three types of matrices show a similar trend.
Figure 4B:
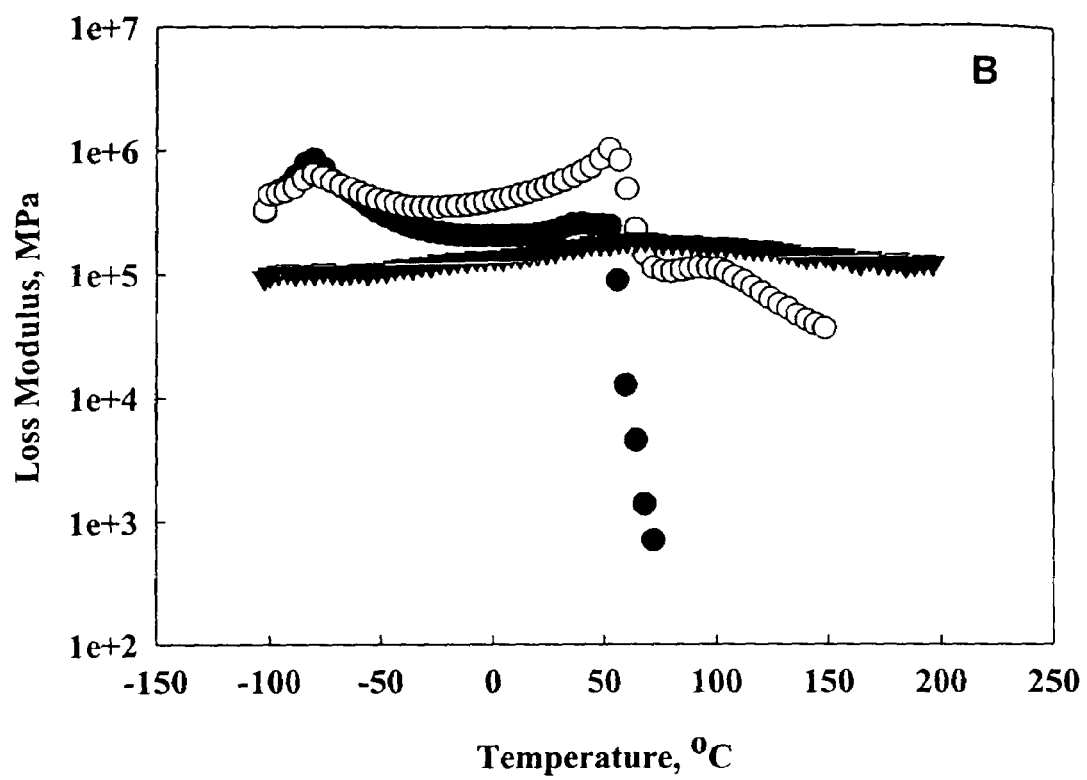
Figure 4C:
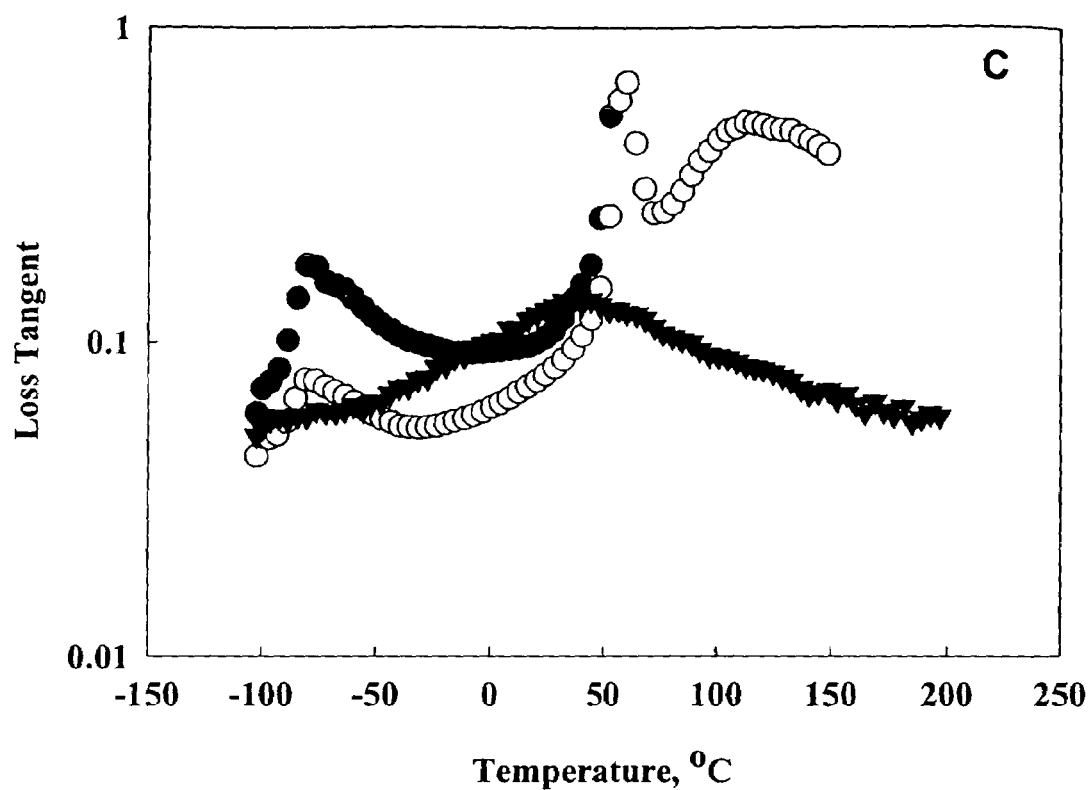

Dynamic mechanical properties of pectin/p(LGA) matrices: Dynamic mechanical analysis (DMA) is a useful complement to microscopic methods for morphology and microstructure investigations of polymeric composites. The dynamic mechanical properties of the pectin/p(LGA) composite matrix and p(LGA) matrix were determined by measuring their compressive storage modulus (E'), loss modulus (E"), and loss tangent (tan d). Typical compressive curves are compared for each sample in FIG. 4, along with curves for the pectin alone. The p(LGA) matrix exhibited a noticeable drop in storage modulus starting at about −80° C. which then plateau by about −40° C. It also had a sharp glass transition at about 50° C., which is consistent with the data obtained from the supplier. Above this temperature the sample no longer gave any force readings on the instrument. A sharp peak at about −80° C. was seen in the loss modulus curve and the loss tangent curve. The overall trends for the pectin/p(LGA) composite curves are similar to those for p(LGA) curves. Nevertheless, significant differences were noted. The pectin/p (LGA) composite showed a much smaller decline in storage modulus over the −80° C. to −40° C. range, and had a higher value for the storage modulus over the entire temperature range. It too showed the glass transition at about 50° C. However, above this temperature the sample still maintained several grams of residual force, whereas the p(LGA) alone retained virtually none. The −80° C. peak in the loss modulus was also still visible in the composite, although it was much smaller than in the p(LGA) matrix, and seemed to be smaller than what would be expected from compositional differences alone.

The curves for plain pectin matrices were relatively flat and were comparable to DMA curves obtained for neat pectin films undergoing small deformation dynamic stretching motion [24]. Pectin undergoing dynamic small deformation compression had lower values of storage modulus and loss modulus than the other two matrices below 50° C. However, at about 50° C. the curves for pectin/p(LGA) and p(LGA) matrices had dropped to below the value of the pectin matrix.

The loss tangent behavior of pectin/p(LGA) and p(LGA) matrices was similar to that seen with the loss modulus, although the difference in the peak size at −80° C. was more striking. The pectin curve showed a broad peak at about 30° C.

Based on these data, it appears that the presence of the pectin raises the mechanical stiffness of the matrix above that of the p(LGA) matrix by itself at temperatures below the glass transition. Above the glass transition, the pectin seems to enable the matrix to maintain some level of physical integrity, although this is at a much lower level than for the matrix at temperature below the glass transition. The incorporation of the pectin network structure seems to be primarily responsible for the increase in the values for E0 and for the decrease in the tan values for the pectin/p(LGA) composite matrix compared to the p(LGA) matrix. These differences are considered to be the contribution of the well-organized double-network structure of the composite matrices, where the thermoplastic p(LGA) networks were reinforced by the non-thermoplastic pectin networks. The presence of the pectin in the matrix was instrumental in limiting molecular motion of p(LGA) polymers with increasing temperature.

Figure 3:
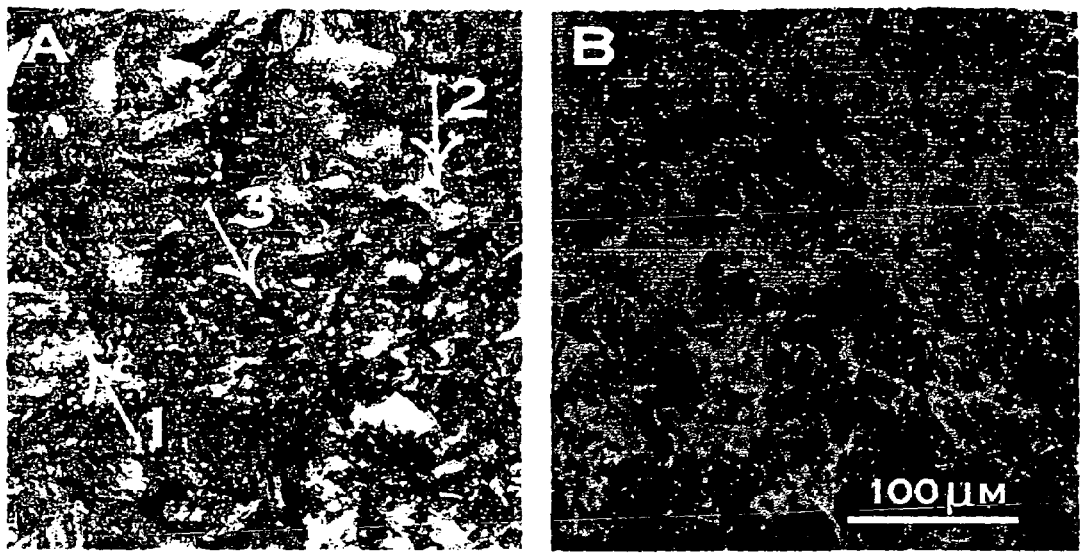
FIG. 3 shows (A) averaged confocal reflection images in stereo-projection of pectin/p(LGA) indicating pectin domains constructed with irregular flat sheets with mid-line ridges or small flat patches (1), p(LGA) domains of fine network of anastomosing fibers (2), and the areas of both (3), (B) Laser confocal micrograph of fluorescently labeled pectin/p(LGA) showing the fluorescence located in pectin areas, not in p(LGA) areas (bar=100 mm).

Characterization of pectin/p(LGA) matrices as carriers of signal molecules: Pectin/p(LGA) matrices were evaluated as carriers of signal molecules by conjugating the matrix with fluoresceinamine (FIG. 3). Green fluorescence was localized in irregular sheets and patches (FIG. 3B). These fluorescent structures were similar to those revealed by SEM for pectin/p(LGA) composite matrices (FIG. 2B), indicating the graft of the fluoresceinamine in pectin areas. Fluorescence was absent from the p(LGA) areas of fibrillar networks in the composite matrices (cf. FIGS. 3A and B). This was consistent with the lack of fluorescent emission observed for p(LGA) matrices (data not shown), indicating the inert nature of p(LGA) to the immobilization reaction. The signal molecules of fluoresceinamine were conjugated directly to the sugar rings of pectin via the activation of the hydroxyl groups of the pectins. The hydroxyl groups of carbohydrate molecules are only mildly nucleophilic, approximately equal to water in their relative nucleophilicity. Thus, the activation of pectins was performed in dry acetone to form intermediate reactive derivatives containing good leaving groups for nucleophilic substitution. The reaction of activated hydroxyls with nucleophiles was conducted in PBS (pH 7.8) at room temperature, which resulted in stable covalent bonds between the carbohydrate and the amine-containing molecules. Tresyl chloride has been demonstrated to be a useful tool to conjugate various peptides and proteins with synthetic polymers or natural polymers. Nevertheless, we observed some loss in matrix integrity in the current experiment, especially when the matrices were treated with dry acetone and during the repeated washing process; without being bound by theory, it may be due to the differences in swellability between the two networks with medium changes.

Figure 5A:
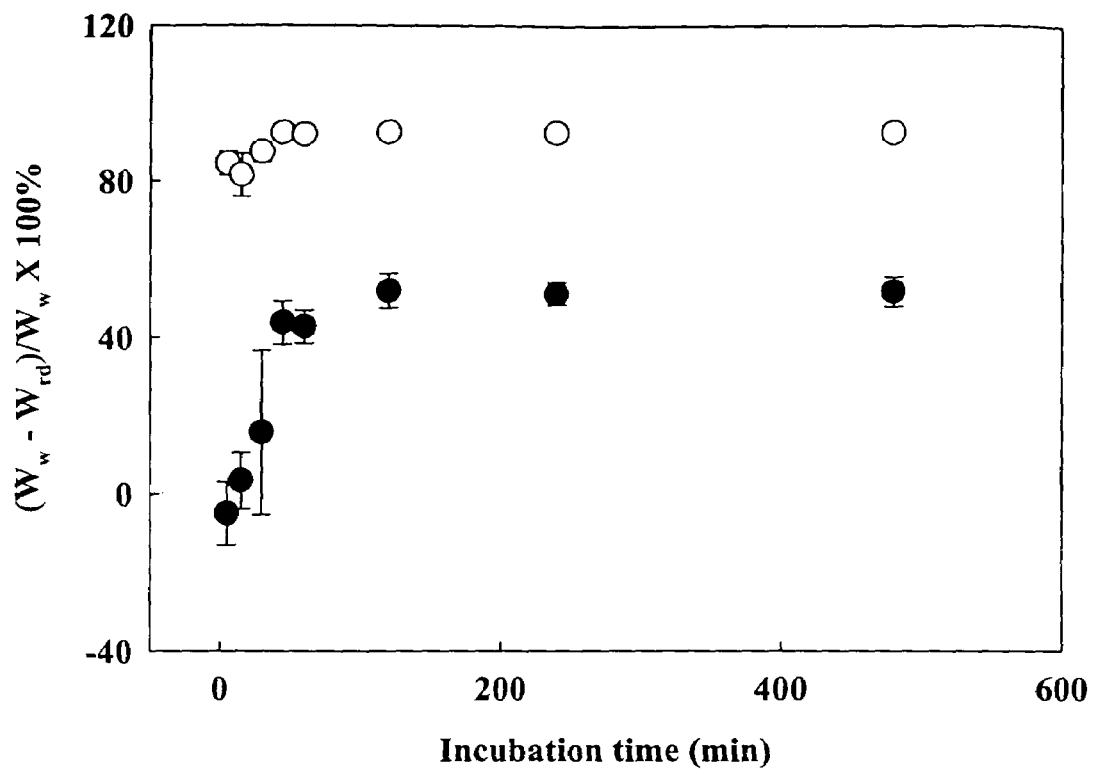
FIG. 5 shows time curves of water adsorption (A) and protein adsorption (B) in pectin/p(LGA) matrix (○) and p(LGA) matrix (•), the experiments were conducted at room temperature using PBS as an incubation media, the protein concentration in PBS was 0.1%, w/v.
Figure 5B:
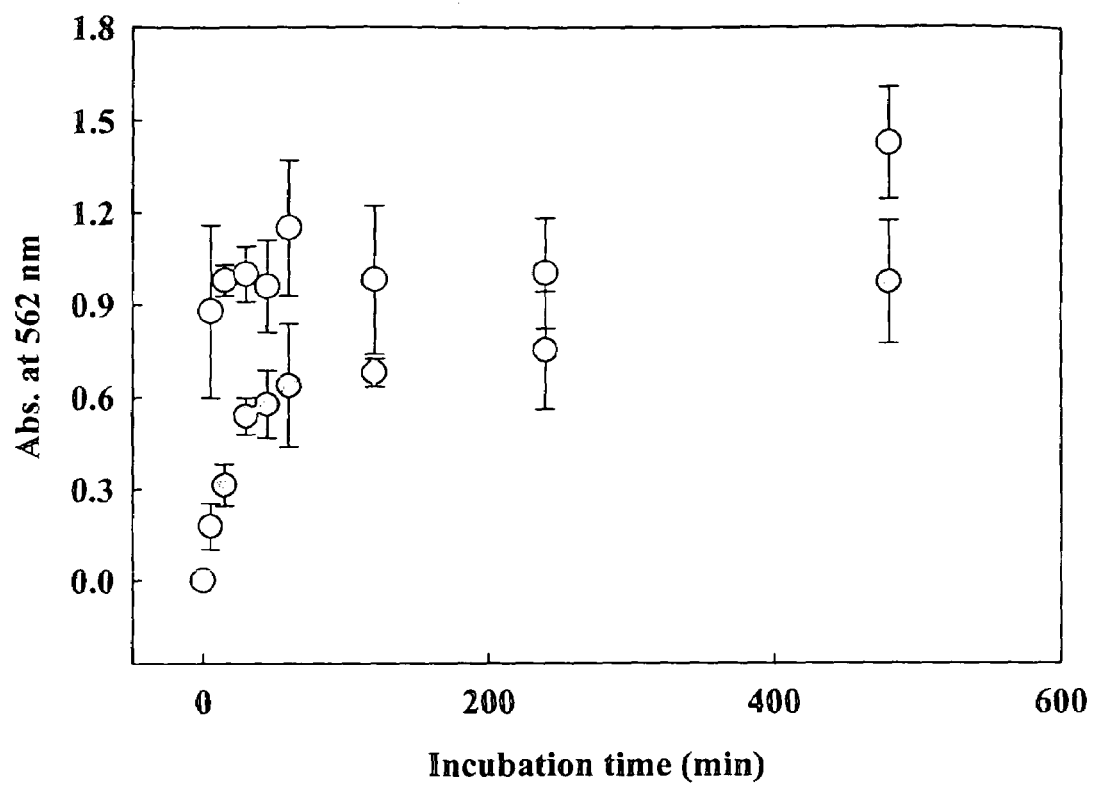
Figure 6:
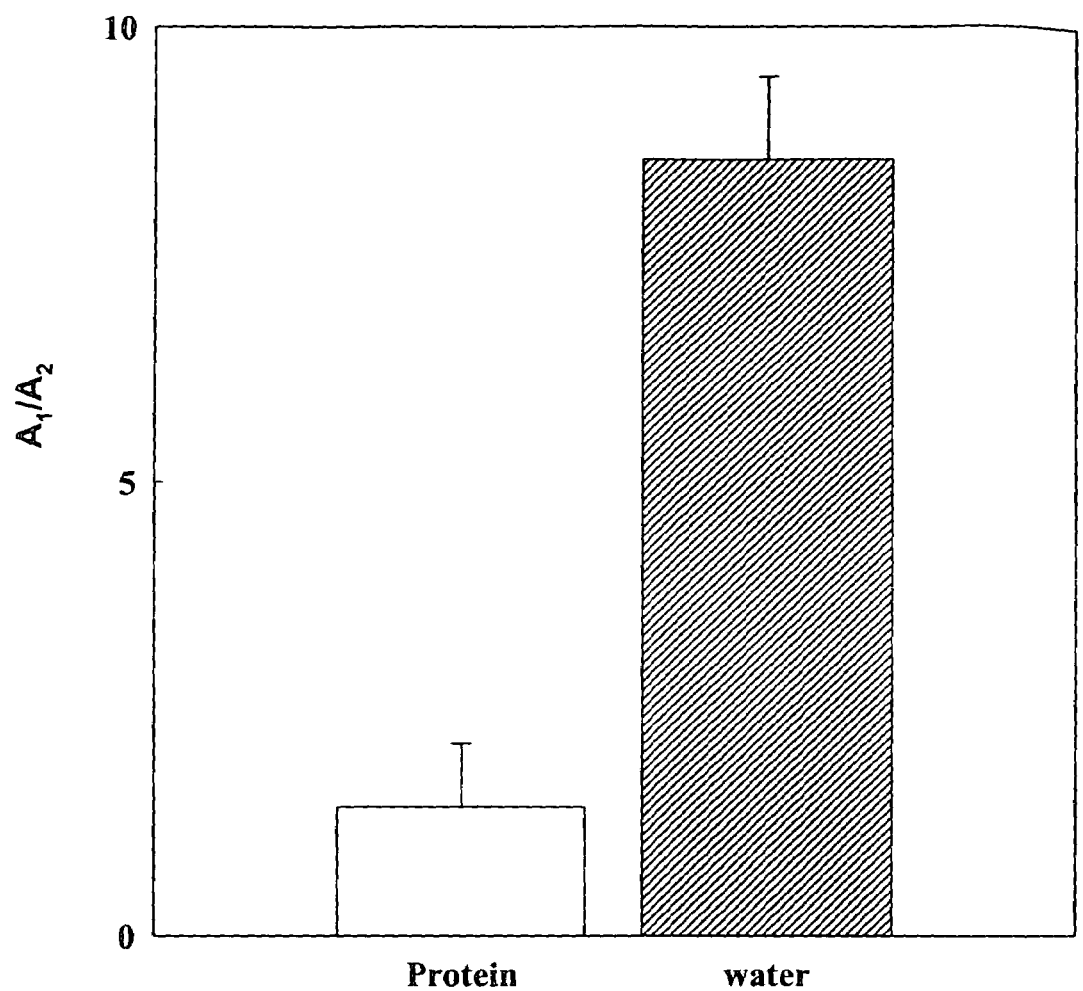
FIG. 6 shows comparison of pectin/p(LGA) to p(LGA) matrices in water/protein adsorption; $A_1$ and $A_2$, the amount of adsorbates detected at equilibrium in pectin/p(LGA) and p(LGA) matrices, respectively.

Since most signal molecules are environmentally sensitive, the incorporation of signal molecules into biomedical devices is often done under very mild conditions such as in aqueous media, at neutral solution pH, and at 37° C. or lower. We evaluated the potential for composite matrices to adsorb signal molecules from aqueous solution by measuring the equilibrium water content and the amount of adsorbed protein. The total water content of matrices was determined by swelling samples of each matrix in PBS and measuring the increase in weight at each incubation time point (FIG. 5A). There was an increase in the water content with the incubation time for both types of matrices. Due to the inclusion of a hydrophilic network, pectin/p(LGA) matrices facilitated water diffusion and uptake into the matrices, as demonstrated by a quick increase in matrix weight at the beginning of incubation. Less time is required to reach equilibrium, and a higher percentage of water adsorbed over the entire time of incubation in comparison with p(LGA) matrices. At steady state, the water content of pectin/p(LGA) composite matrices was about eight-fold of that of p(LGA) matrices (FIG. 6). For protein adsorption, there was a trend similar to water uptake for both pectin/p(LGA) and p(LGA) matrices (FIG. 5B). As in the case of water, the pectin/p(LGA) matrix adsorbed more protein than the p(LGA) matrix (FIG. 6). However, the adsorbed BSA found in pectin/p(LGA) matrices was only 1.5-fold of that detected in p(LGA) matrix (FIG. 6). For p(LGA) matrices, both water and BSA are only able to diffuse to and remain in pore spaces of the matrices. In pectin/p(LGA) matrices, small molecules of water not only diffused and remained in the pore spaces, but also penetrated into the pectin gel domains. Compared to water penetration, only a small fraction of protein BSA was capable of penetrating to the pectin domains. These results demonstrated the capability of pectin/p(LGA) composite matrices to carry signal molecules either by chemical conjugation or by physical adsorption.

Figure 7:
FIG. 7 shows osteoblast distribution in pectin/p(LGA) matrices (top panel) and p(LGA) matrices (bottom panel) after 1 day cell seeding (the samples were stained using hematoxylin and eosin), there were more osteoblasts (arrow head) in pectin/p(LGA) matrices than in p(LGA) matrices (magnification: A (40×) and B (200×)).
Figure 8:
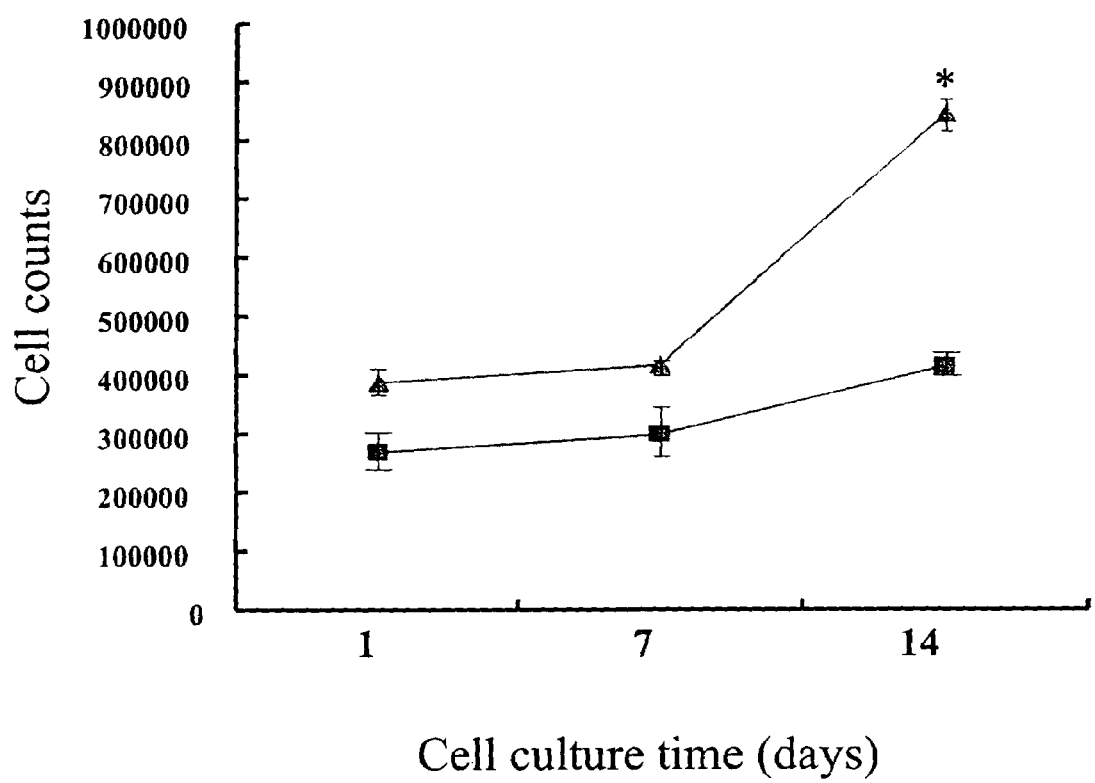
FIG. 8 shows in vitro osteoblast proliferation on (▲) pectin/p(LGA) and (■) p(LGA) matrices versus cultivation time, one million cells were seeded onto each matrix, P<0:01.

In vitro cell culture: After 1 day of cell seeding, osteoblasts were attached onto pectin/p(LGA) and p(LGA) matrices. There were more cells on pectin/p(LGA) matrices than on p(LGA) matrices. Furthermore, histological analysis revealed that osteoblasts attached to pectin/p(LGA) matrices in multi-layers whereas they attached to p(LGA) matrices in a single layer (FIG. 7). Cells were not only attached on these matrices, but were also viable and had the capability to proliferate (FIG. 8). Although the difference in cell number was not statistically significant at the beginning, after 2 weeks culture, cell numbers on the pectin/p(LGA) matrices were two-fold of that on the p(LGA) matrices (FIG. 8).

Conclusions: We have presented a method to effectively combine synthetic polymers (e.g., p(LGA)) and natural polymers (e.g., pectin) in one matrix. By including dry particles of pectins and calcium chloride in p(LGA)/chloroform solution, composite matrices were created with an interconnected porous morphology. The composite matrices consisted of a pectin network reinforced by a p(LGA) network. The composite matrices combined the best features of both polymers. Typically, the mechanical properties of the composite were comparable to p(LGA) whereas their capacity to hold water and accessibility to proteins were comparable to pectin. In addition, the composite matrices provided side chain functional groups for further chemical modifications, which could be used in various biomedical applications. As demonstrated by in vitro cell culture, the composite matrices show promise for tissue engineering applications. Thus, by selecting a group of synthetic polymers with appropriate pairs of inorganic salts and polysaccharides, many polymeric composite matrices can be created by this simple and environmentally friendly method.

Thus, in one aspect, the method described herein for producing the matrices is a one step process for creating pores and chemical cross-links in a pectin-based material by pre-loading $CaCl_2$ salts into the precursor suspension of pectin/p(LGA). The resulting pectin/p(LGA) composites possess a series of unique features different from matrices of p(LGA) alone. Namely, these composites allow hydrophilic substances to access and affiliate to them. This feature is important in preparing carriers for protein delivery: DNA therapeutics, implants for tissue repair, and other health care products. In these applications, devices prepared from p(LGA) alone lacked efficacy due to their hydrophobic nature. It is expected that pectin/p(LGA) composites will be useful delivery vehicles for a larger number of protein drugs, which are organic solvent sensitive.

Example 2

Matrix preparation using pectin and poly(lactide-co-glycolide)(p(LGA)). Pectin was dissolved in D.I. water at the concentration of 1-50 mg/ml; p(LGA) was dissolved in dichloromethane at 10-200 mg/ml; the two solutions were mixed at the volume ratio of 1/10 or 10/1 (pectin: p(LGA)) by vortexing. The mixture was poured into a mold, which was pre-cooled at the temperature lower than −75° C. (using liquid nitrogen or the mixture of dry ice and isopropyl alcohol). After the slurry was frozen, the mold was transferred into a desiccator which was placed in an icebox containing dry ice (−56.6° C.) and connected to a vacuum line. The icebox was evacuated for 8 hrs at −56.6° C., followed by 12 hrs in lyophilizer at −10° C.

All of the references cited herein are incorporated by reference in their entirety. Also incorporated by reference in their entirety are the following references: BeMiller, J. M., An introduction to pectins: structure and properties, In: Chemistry and function of pectins, ACS series 310, M. L. Fishman and J. J. Jen, editors, American Chemical Society, Washington, D.C., 1986, p. 2-13; Berhold, et al., J. Cont.r Rel., 39:17-25 (1996); Bodmeier, R., and O. Paeratakul, Pharm. Res., 11:882-888 (1994); Carson, F. L., Histotechnology: a self instructional text, ASCP Press, Chicago, Ill., 1990; Chen, et al., Science, 276:1425-1428 (1997); Coffin, D. R., et al., J. Appl. Polym. Sci., 61:71-79 (1996); Dickerson, K. T., et al., U.S. Pat. No. 5,677,276; Dubois, M., et al., Anal. Chem., 28: 350-356 (1956); Fishman, M. L., et al., Carbohydrate Res., 5:359-379 (2000); Fishman, M. L., et al., J. Agr. Food Chem., 49: 4494-4501 (2001); Freed, et al., J. Biomed. Mater. Res., 27:11-23 (1993); Hwang, J., and J. L. Kokini, J. Texture Stud., 22: 123-167 (1991); Ishaug et al., J. Biomed. Mater. Res., 36:17-28 (1997); Kim, J. H., and R. Fassihi, J. Pharm. Sci., 86(3): 316-328 (1997); Langer, R., J. P. Vacanti, Science, 260: 920-926 (1993); Lanza, R. P., et al., Principles of tissue engineering, Academic Press, San Diego, Calif., 1997; Liu, L. S., and R. A. Berg, J. Biomed. Mater. Res. (Appl. Biomater.), 63: 326-332 (2002); Liu, L. S., et al., Biomaterials, 24: 3333-3343 (2003); Liu, L. S., et al., Conversion of Pectin and Related Polysaccharides into Unique Biomaterials for Biomedical Applications, Proceedings of the United States-Japan UJNR Cooperative Program in Natural Resources and Agriculture Panel, 32$^{nd}$ Annual Meeting, Tsukuba, Ibaraki, Japan, Nov. 9-15, 2003, pages 405-409; Liu, L. S., et al., Biomaterials, 25: 3201-3210 (2004); Ma, P. X., and R. Langer, Fabrication of biodegradable polymer foams for cell transplantation and tissue engineering, In: Tissue engineering methods and protocols, J. Morgan and M. Yarmush, editors, Humana Press Inc., Totowa, N.J., 1999, p. 47-56; Ma, P. X., et al., J. Biomed. Mater. Res., 54(2): 284-293 (2001); Massia, S. P., and J. A. Hubbell, Anal. Biochem., 187: 292-301 (1990); Mikos, et al., J. Biomed. Mater. Res., 27:183-189 (1993); Mikos, A. G., et al., Polymer, 35(5): 1068-1077 (1994); Nilsson, K., and K. Mosbach, Biochem. Biophys. Res. Comm., 102(1): 449-457 (1981); Ouchi, T. et al, Macromolecules, 3(5): 885-888 (2002); Patrick, C. W., et al., editors, Frontiers in tissue engineering, Pergamon, N.Y., 1998; Rubinstein, A., et al., Pharm. Res., 10(2): 258-263 (1993); Schols, H. A., and A. G. J. Voragen, Complex pectins: structure elucidation using enzymes, In: Pectin and pectinases, J. Visser and A. G. J. Vorangen, editors, Elsevier Science, Amsterdam, 1996, p. 3-19; Semde, R., et al., Int. J. Pharm., 197: 181-92 (2000); Smith, P. K., Anal. Biochem., 150: 76-85 (1985); Temenoff et al., Biomaterials, 21:431-440 (2000); and Voragen, A. G. J., et al., Food Hydrocolloids, 1: 65-70 (1986).

Also incorporated by reference in their entirety are the following U.S. Pat. Nos. 4,060,081; 5,041,138; 5,514,378; 5,744,516; 5,817,728; 6,010,870; 6,114,496; 6,124,384; 6,150,438; 6,207,749; 6,294,202; 6,326,021; 6,350,531; 6,379,962; 6,388,047; 6,399,700; and 6,423,345.

Thus, in view of the above, the present invention concerns (in part) the following:

A porous polymeric matrix (polymeric composition) comprising (or consisting essentially of or consisting of) at least one natural polymer and at least one synthetic polymer and optionally at least one cation.

The above porous polymeric matrix, wherein said synthetic polymer is selected from the group consisting of polyesters, polyanhydrides, polyortho esters, and mixtures thereof.

The above porous polymeric matrix, wherein said polyester is selected from the group consisting of poly(lactic acid), poly(glycolic acid), poly(lactic acid-co-glycolic acid), poly (lactide), poly(glycolide), poly(lactide-co-glycolide), polycaprolactone, poly(lactide-co-caprolactone), and mixtures thereof.

The above porous polymeric matrix, wherein said polyester is poly(lactide-co-glycolide) or polycaprolactone.

The above porous polymeric matrix, wherein said poly (lactide-co-glycolide) has a MW from about 500 to about 10,000,000 Da.

The above porous polymeric matrix, wherein said poly (lactide-co-glycolide) has a MW from about 2,000 to about 1,000,000 Da.

The above porous polymeric matrix, wherein said poly (lactide-co-glycolide) has a MW from about 500 to about 5,000 Da.

The above porous polymeric matrix, wherein said poly (lactide-co-glycolide) has a LA:GA ratio of from about 75:25 to about 85:15 (mol:mol).

The above porous polymeric matrix; wherein said polyanhydride is selected from the group consisting of poly(carboxyphenoxy propane-sebacic acid), poly(1,6-bis(p-carboxyphenoxy)hexane, poly(anhydride-co-imide), and mixtures thereof.

The above porous polymeric matrix, wherein said polyortho ester is selected from the group consisting of ALZAMER, CHRONOMER, copolymers of ALZAMER or CHRONOMER with poly(lactide-co-glycolide) or polyethylene glycol, and mixtures thereof.

The above porous polymeric matrix, wherein said natural polymer is pectin.

The above porous polymeric matrix, wherein said pectin has a MW from about 500 to about 1,000,000 Da.

The above porous polymeric matrix, wherein said pectin has a MW from about 230,000 to about 280,000 Da.

The above porous polymeric matrix, wherein said pectin has a MW of about 3000 Da.

The above porous polymeric matrix, wherein said pectin has a DE from about 10 to about 100%.

The above porous polymeric matrix, wherein said pectin has a DE from about 25 to about 76%.

The above porous polymeric matrix, wherein said pectin has a DE from about 25 to about 35%.

The above porous polymeric matrix, wherein said porous polymeric matrix does not contain a cation.

The above porous polymeric matrix, wherein said porous polymeric matrix contains at least one cation.

The above porous polymeric matrix, wherein said cation is selected from the group consisting of calcium, sodium, magnesium, ammonium, and mixtures thereof.

The above porous polymeric matrix, wherein said cation is selected from the group consisting of calcium, sodium, and mixtures thereof.

A method of making a porous polymeric matrix, comprising (or consisting essentially of or consisting of) mixing at least one natural polymer and inorganic salts with a solution comprising (or consisting essentially of or consisting of) at least one solvent and at least one synthetic polymer to form a slurry, casting said slurry in a mold and removing said solvent to form solid matrices, immersing said solid matrices in deionized water to allow natural polymer cross-linking and pore creation to occur simultaneously, and drying said matrices to create a porous polymeric matrix; wherein said porous polymeric matrix comprises at least one natural polymer and at least one synthetic polymer and at least one cation.

The above method, wherein the ratio of said salt particles and said natural polymer to said synthetic polymer is about 1:1 to about 40:1.

The above method, wherein said inorganic salts are selected from the group consisting of calcium chloride, sodium chloride, magnesium chloride, sodium sulfate, potassium sulfate, ammonium sulfate, ammonium chloride, potassium chloride, and mixtures thereof.

The above method, wherein the ratio of said natural polymer to said inorganic salts is from about 1:about 0.1-about 20.

The above method, wherein the ratio of said natural polymer to said synthetic polymer is from about 0.1:about 99.9 to about 99.9: about 0.1.

The above porous polymeric matrix, wherein said porous polymeric matrix is made by the above method.

The above porous polymeric matrix, wherein said porous polymeric matrix is made by the method below.

A porous polymeric matrix comprising (or consisting essentially of or consisting of) at least one natural polymer and at least one synthetic polymer and at least one cation, wherein said porous polymeric matrix is made by a method comprising (or consisting essentially of or consisting of) mixing at least one natural polymer and inorganic salts with a solution comprising at least one solvent and at least one synthetic polymer to form a slurry, casting said slurry in a mold and removing said solvent to form solid matrices, immersing said solid matrices in deionized water to allow natural polymer cross-linking and pore creation to occur simultaneously, and drying said matrices to create a porous polymeric matrix.

A method of making a porous polymeric matrix, comprising (or consisting essentially of or consisting of) mixing at least one natural polymer in an aqueous solvent and mixing at least one synthetic polymer in an organic solvent, combining the mixtures and casting in a mold, and separately removing said aqueous solvent and said organic solvent to form a porous polymeric matrix; wherein said porous polymeric matrix comprises at least one natural polymer and at least one synthetic polymer and does not contain a cation.

A porous polymeric matrix comprising (or consisting essentially of or consisting of) at least one natural polymer and at least one synthetic polymer, wherein said porous polymeric matrix is made by a method comprising (or consisting essentially of or consisting of) mixing at least one natural polymer in an aqueous solvent and mixing at least one synthetic polymer in an organic solvent, combining the mixtures and casting in a mold, and separately removing said aqueous solvent and said organic solvent to form a porous polymeric matrix; wherein said porous polymeric matrix does not contain a cation.

A method for making an osteoblast containing porous polymeric matrix, comprising (or consisting essentially of or consisting of) providing the above porous polymeric matrix in a nutrient environment and attaching osteoblast cells to said porous polymeric matrix to form an osteoblast containing porous polymeric matrix suitable for implantation into a patient to replace defective or missing bone.

A method for engineering tissue comprising (or consisting essentially of or consisting of) growing cells on the above porous polymeric matrix.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Molecular properties of pectins

| Properties | De-esterification | |
|---|---|---|
| | Before | After |
| Mw × $10^{-5}$ | 0.87 (0.02) | 0.81 (0.01) |
| Rgz (nm) | 24.7 (2.06) | 21.4 (0.06) |
| $[\eta]_w$ (dL/g) | 1.25 (0.02) | 1.22 (0.02) |
| DE (%) | 93 | 10.2 (0.77) |

TABLE 2

Physical characterization of pectin/p(LGA) and p(LGA) matrices

| Matrices | Density (g/ml) | Pectin content (mg) | | P(LGA) content (mg) | |
|---|---|---|---|---|---|
| | | calculated | determined | calculated | determined |
| Pectin/p(LGA) | 0.190 | 1.28 | 1.06 ± 0.2 | 12.8 | 11.4 ± 3.2 |
| P(LGA) | 0.306 | N/A | N/A | 26.0 | 24.8 ± 2.4 |

We claim:

1. A method of making a porous polymeric matrix, comprising mixing at least one natural polymer and inorganic salts with a solution comprising at least one solvent and at least one synthetic polymer to form a slurry, casting said slurry in a mold and removing said solvent to form solid matrices, immersing said solid matrices in deionized water to allow natural polymer cross-linking and pore creation to occur simultaneously, and drying said matrices to create a porous polymeric matrix; wherein said porous polymeric matrix comprises at least one natural polymer and at least one synthetic polymer and at least one cation.

2. The method according to claim 1, wherein the ratio of said salt particles and said natural polymer to said synthetic polymer is about 1:1 to about 40:1.

3. The method according to claim 1, wherein said inorganic salts are selected from the group consisting of calcium chloride, sodium chloride, magnesium chloride, sodium sulfate, potassium sulfate, ammonium sulfate, ammonium chloride, potassium chloride, and mixtures thereof.

4. The method according to claim 1, wherein the ratio of said natural polymer to said inorganic salts is from about 1:about 0.1-about 20.

5. The method according to claim 1, wherein the ratio of said natural polymer to said synthetic polymer is from about 0.1:about 99.9 to about 99.9:about 0.1.

6. A porous polymeric matrix comprising at least one natural polymer and at least one synthetic polymer and at least one cation, wherein said porous polymeric matrix is made by a method comprising mixing at least one natural polymer and inorganic salts with a solution comprising at least one solvent and at least one synthetic polymer to form a slurry, casting said slurry in a mold and removing said solvent to form solid matrices, immersing said solid matrices in deionized water to allow natural polymer cross-linking and pore creation to occur simultaneously, and drying said matrices to create a porous polymeric matrix.

7. The porous polymeric matrix according to claim 6, wherein said cation is selected from the group consisting of calcium, sodium, magnesium, ammonium, and mixtures thereof.

8. The porous polymeric matrix according to claim 6, wherein said cation is selected from the group consisting of calcium, sodium, and mixtures thereof.

9. The porous polymeric matrix according to claim 1, wherein said synthetic polymer is selected from the group consisting of polyester, polyanhydride, polyortho ester, and mixtures thereof.

10. The porous polymeric matrix according to claim 9, wherein said polyester is selected from the group consisting of poly(lactic acid), poly(glycolic acid), poly(lactic acid-co-glycolic acid), poly(lactide), poly(glycolide), poly(lactide-co-glycolide), polycaprolactone, poly(lactide-co-caprolactone), and mixtures thereof.

11. The porous polymeric matrix according to claim 10, wherein said polyester is poly(lactide-co-glycolide).

12. The porous polymeric matrix according to claim 11, wherein said poly(lactide-co-glycolide) has a MW from about 500 to about 10,000,000 Da.

13. The porous polymeric matrix according to claim 11, wherein said poly(lactide-co-glycolide) has a MW from about 2,000 to about 1,000,000 Da.

14. The porous polymeric matrix according to claim 11, wherein said poly(lactide-co-glycolide) has a MW from about 500 to about 5,000 Da.

15. The porous polymeric matrix according to claim 11, wherein said poly(lactide-co-glycolide) has a LA:GA ratio of from about 75:25 to about 85:15 (mol:mol).

16. The porous polymeric matrix according to claim 9, wherein said polyanhydride is selected from the group consisting of poly(carboxyphenoxy propane-sebacic acid), poly(1,6-bis(p-carboxyphenoxy)hexane), poly(anhydride-co-imide), and mixtures thereof.

17. The porous polymeric matrix according to claim 9, wherein said polyortho ester is selected from the group consisting of ALZAMER, CHRONOMER, copolymers of ALZAMER or CHRONOMER with poly(lactide-co-glycolide) or polyethylene glycol, and mixtures thereof.

18. The porous polymeric matrix according to claim 10, wherein said polyester is polycaprolactone.

* * * * *